United States Patent [19]

Ozawa et al.

[11] 4,251,662
[45] Feb. 17, 1981

[54] PHENOXYPYRIDINE DERIVATIVES

[75] Inventors: Kiyomi Ozawa; Shigeru Ishii; Masataka Hatanaka, all of Funabashi, Japan

[73] Assignee: Nissan Chemical Industries, Limited, Tokyo, Japan

[21] Appl. No.: 107,937

[22] Filed: Dec. 28, 1979

[30] Foreign Application Priority Data

Dec. 29, 1978 [JP] Japan .............................. 53/163083

[51] Int. Cl.³ .......................................... C07D 213/79
[52] U.S. Cl. ..................................................... 546/301
[58] Field of Search ........................................ 546/301

[56] References Cited
PUBLICATIONS

Boekelheide et al., Journal of American Chemical Society, vol. 76, pp. 1286–1291, (1954).

*Primary Examiner*—Alan L. Rotman
*Attorney, Agent, or Firm*—Oblon, Fisher, Spivak, McClelland & Maier

[57] ABSTRACT

A phenoxypyridine derivative having the formula $(CH_3COO)_nCH_{3-n}R$  (I)

wherein R represents

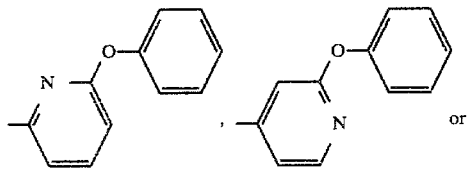

-continued

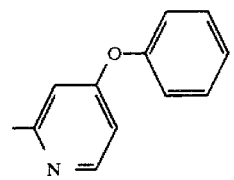

and n is 1 or 2 is produced by reacting a phenoxypyridine-N-oxide derivative having the formula $(CH_3COO)_{n-1}CH_{4-n}R'$  (III)

wherein R' represents

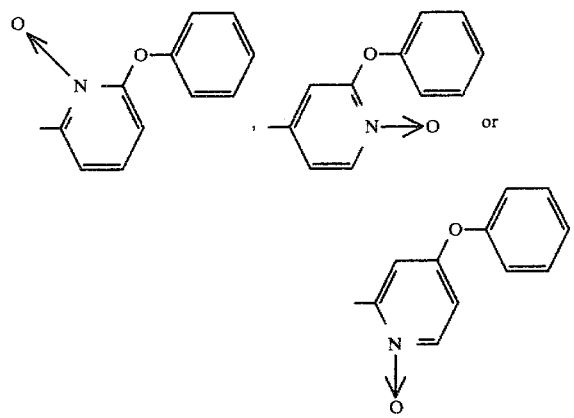

and n is 1 or 2 with acetic anhydride.

The phenoxypyridine derivatives are especially suitable for producing synthetic pyrethroids having excellent insecticidal and acaricidal activity in high yield and an economical process.

4 Claims, No Drawings

PHENOXYPYRIDINE DERIVATIVES

BACKGROUND OF THE INVENTION

1. Field of the Invention

The present invention relates to novel phenoxypyridine derivatives which are not known in prior arts and are effective intermediates from which compounds for controlling injurious pests, especially synthetic pyrethroid type insecticidal compounds are effectively produced in a special economical manner.

2. Description of the Prior Arts

Recently, structural modifications of natural pyrethrin have been widely studied and various synthetic pyrethroids such as chrysanthemumic acid ester derivatives and non-chrysanthemumic acid type isovaleric acid derivatives have been practically used as insecticides.

Natural pyrethrin has excellent immediate effect, low mammalian toxicity and low residual effect and are effective as household insecticide, for controlling insect pests in sanitation, however it is not effective as an insecticide in agriculture because of photodecomposition of the compound in natural environment. On the other hand, synthetic pyrethroids have excellent insecticidal effect and residual effect to insect pests in sanitation as well as in agriculture. However, synthetic pyrethorids are not economical in view of costs for productions in comparison with other synthetic compounds such as organic phosphorus and carbamate insecticides. Thus, it has been required to develop new processes for producing synthetic pyrethroids which are advantageous industrial processes.

SUMMARY OF THE INVENTION

It is an object of the present invention to provide novel compounds effective as intermediates for synthetic pyrethroids.

It is another object of the present invention to provide novel compounds from which important synthetic pyrethroids can be effectively produced in a special economical manner.

It is the other object of the present invention to provide a process for producing the novel compounds.

The foregoing and other objects have been attained by providing novel phenoxypyridine derivatives having the formula $$(CH_3COO)_nCH_{3-n}R \quad (I)$$

wherein R represents

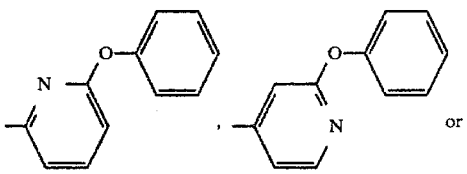

, 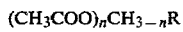 or

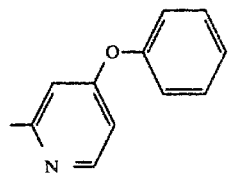

and n is 1 or 2.

DETAILED DESCRIPTION OF THE PREFERRED EMBODIMENTS

The inventors have studied and found that novel phenylcyclopropane carboxylic acid derivatives having the formula (V) have excellent insecticidal and acaricidal activities.

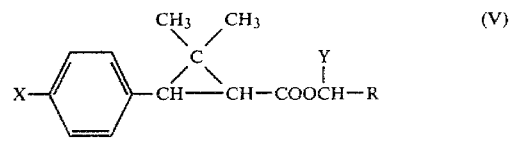

wherein X represents hydrogen or a halogen atom, $C_{1-5}$ alkyl group $C_{1-5}$ alkoxy group, trifluoromethyl, cyclopropyl, tri-lower alkylsilyl, lower alkylthio or cyano; Y represents hydrogen atom, or cyano group; and R is defined above.

The phenylcyclopropane carboxylic acid derivatives are new type synthetic pyrethroids having a phenoxypyridine skeleton and can be produced by the following reactions.

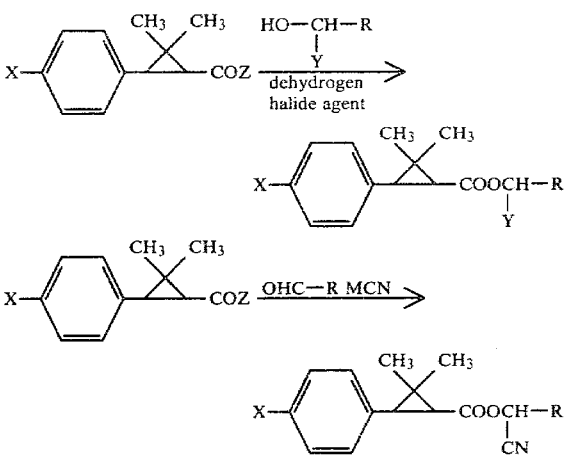

wherein X, Y and R are defined above and M represents Na or K; Z represents a halogen atom or a substituted sulfonic acid group.

Thus, it has not been known to provide industrial advantageous processes for producing phenoxypyridinemethanols, cyano(phenoxypyridine)methanol or phenoxypicolinic aldehydes which are used for said reactions.

The following processes have been proposed in Japanese Unexamined Patent Publication No. 112881/1978.

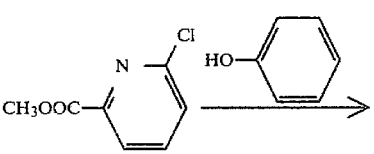

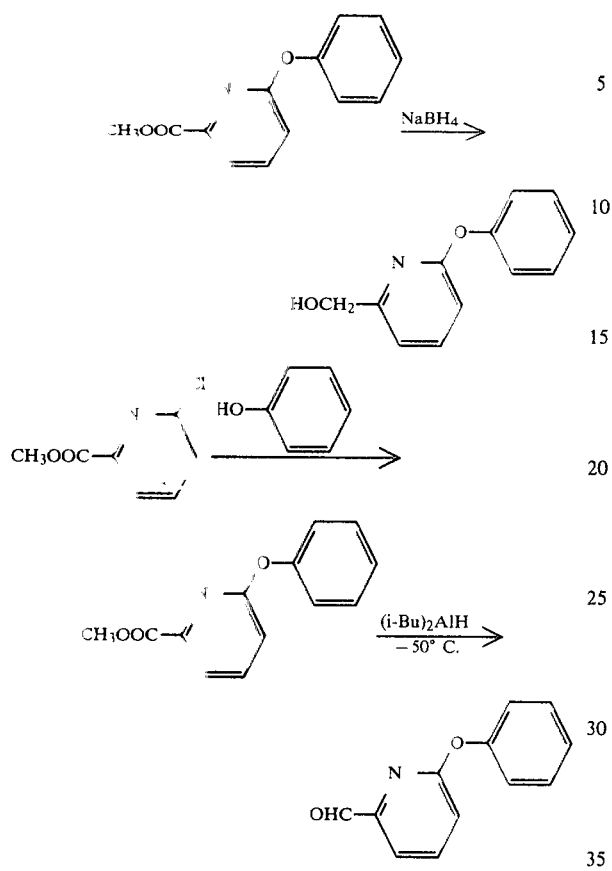

In said reactions, the starting material of, methyl 6-chloropicolinate and the reducing agent of sodium borohydride or diisobutyl aluminum hydride are expensive reagents. In the latter reaction for producing the aldehyde, the reaction is carried out at low temperature such as −50° C. The process for the reaction is not an effective industrial process.

In accordance with the process of the present invention, the object compounds having high purity can be produced by using economical starting materials and the reagents by simple operations in high yield.

The process for producing the novel phenoxypyridine derivatives of the present invention is shown by the reaction formulas (A) and (B).

$$(CH_3COO)_{n-1}CH_{4-n}R \xrightarrow{\text{oxidizing agent}} (CH_3COO)_{n-1}CH_{4-n}-R' \quad (A)$$

$$(CH_3COO)_{n-1}CH_{4-n}R' \xrightarrow{(CH_3CO)_2O} (CH_3COO)_nCH_{3-n}R$$

wherein R and n are defined above; and R' represents

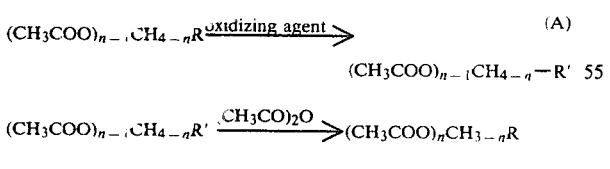

or

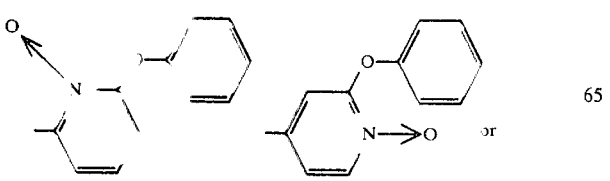

The process for producing the compound of the present invention will be further illustrated.

In the reaction (A), phenoxypicoline or phenoxypyridinemethanol acetate is used as a starting material and an oxidizing agent used for N-oxide for pyridine derivatives is used. The oxidizing agents are disclosed in Pyridine and It's Derivatives (Heterocyclic Compounds) Vol. 14, Suppl. Part 2 page 5-15 by R. A. Abramovitch.

In an industrial process, it is preferable to use a combination of hydrogen peroxide and glacial acetic acid or peracetic acid, or pertrifluoroacetic acid which is economically available.

In the reaction, the oxidizing agent can be used at equimolar ratio to phenoxypicoline or phenoxypyridinemethanol acetate as the starting material. Thus, excess of the oxidizing agent can be used to impart the effect as a solvent.

The reaction is usually carried out at a temperature from room temperature to about 100° C. When the reaction temperature is about room temperature, it takes a long time for completing the reaction. Thus, it is preferable to carry out the reaction at about 70° to 90° C. so as to complete the reaction for several to ten and several hours.

The N-oxide derivative can be separated from the reaction mixture by conventional separating methods such as condensation, extraction, washing, drying, vacuum distillation and chromatography.

Phenoxypicoline used as the starting material in the reaction (A) can be easily obtained by the following known syntheses or like by using aminopicoline as the starting material.

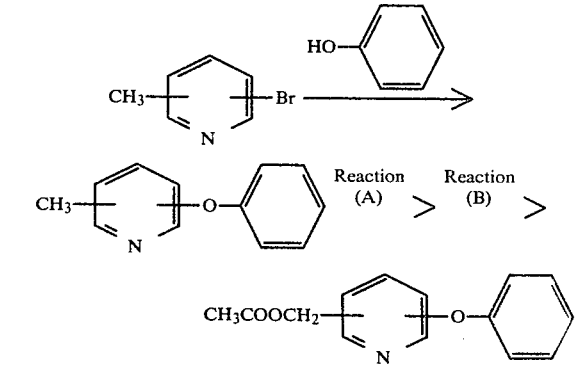

The reaction (B) will be illustrated. The N-oxide derivative obtained by the reaction (A) or the other process can be used as the starting material and acetic anhydride is added to the N-oxide derivative at greater than equimolar ratio. In order to perform a smooth reaction, it is preferable to use about 2 equimole of acetic anhydride to the N-oxide derivative. Excess acetic anhydride imparts as a medium for the reaction. If desired, a polar solvent such as dioxane can be used together with excess acetic anhydride in the reaction. It is also possible to add the other solvent if desired.

It is preferable to carry out the reaction at a temperature from about 50° C. to about the boiling point of the solvent. It is especially preferable to carry out the reaction at higher than 100° C. so as to complete the reaction for several tens minutes. After the reaction, a crude product is obtained by distilling off excess acetic anhydride and acetic acid etc. as the by-product from the reaction mixture. The crude product is purified by the conventional separating method such as vacuum distillation and chromatography.

The structures of the compounds of the present invention produced by said process are shown.

| Compound No. | Structure | |
|---|---|---|
| 1 | (structure) | (VI) |
| 2 | (structure) | (VII) |
| 3 | (structure) | (VIII) |
| 4 | (structure) | (IX) |
| 5 | (structure) | (X) |
| 6 | (structure) | (XI) |

These compounds are novel compounds useful as intermediates for syntheses of synthetic pyrethroids. Compounds No. 1 and No. 2 are especially easily produced in high yield and synthetic pyrethroids obtained by the following method by using said compound as the intermediate have remarkably excellent insecticidal and acaricidal activities.

The reaction formulas in the process for producing phenylcyclopropane carboxylic acid esters by using Compound No. 1 or No. 2 as the typical compounds of the present invention are shown.

Compounds No. 3 to 6 of the present invention can be also converted into the corresponding carboxylic acid esters by the similar reactions.

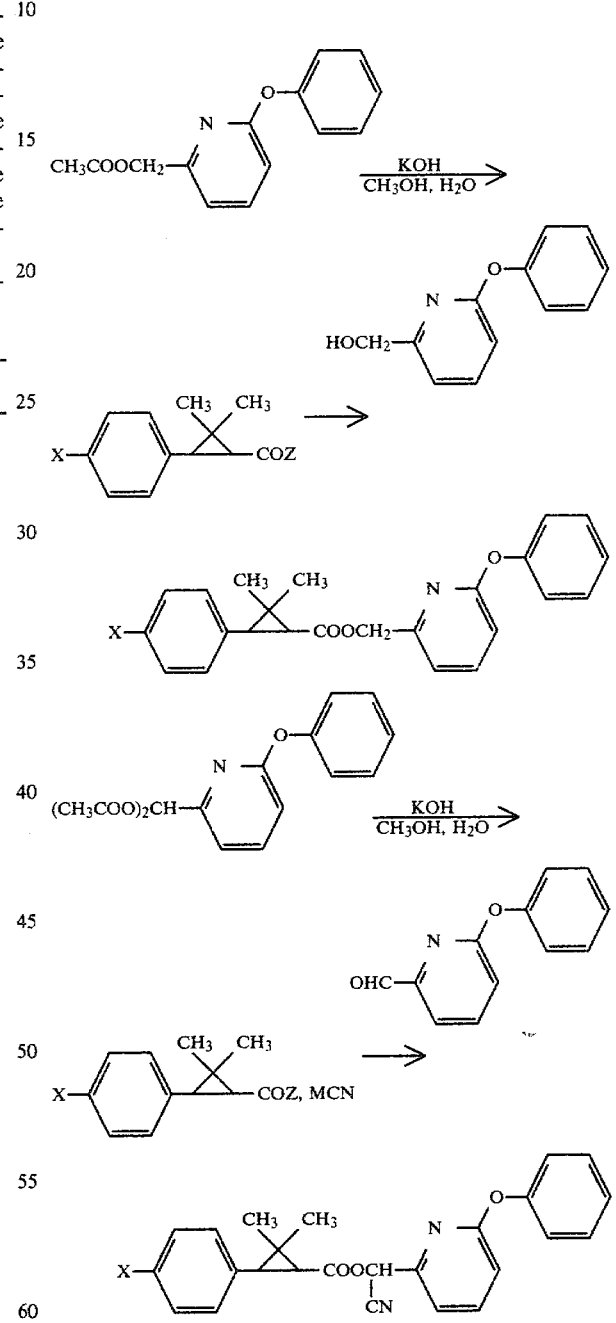

wherein Z is defined above the M represents Na or K.

The phenylcyclopropane carboxylic acid derivatives obtained by the reaction have excellent insecticidal and acaricidal activities to various insect pests in sanitation such as houseflies and mosquito as well as insect pests in agriculture and horticulture which injure rice, vegetables, fruits, cotton and other plants. These effectiveness is described in the prior patent application No. Japanese Patent Application No. 152838/1978.

The phenoxypyridine derivatives of the present invention are effective intermediates from which said insecticidal and acaricidal compounds having high purity can be obtained in high yield. That is, the novel intermediates of the present invention are especially advantageous for producing said insecticidal and acaricidal compounds.

Certain examples of syntheses of the phenoxypyridine derivatives of the present invention will be illustrated.

EXAMPLE 1

Preparation of 6-phenoxypyridine-2-methanol acetate (Compound No. 1: Formula VI)

Into 130 ml of glacial acetic acid, 39.8 g of 6-phenoxy-2-picoline was dissolved and 20 ml of 35% hydrogen peroxide was added and the mixture was stirred at 80° C. for 3 hours to react them and 15 ml of 35% hydrogen peroxide was further added and the mixture was stirred at 80° C. for 9 hours to complete the reaction. After the reaction, the reaction mixture was concentrated under a reduced pressure to be about 50 ml. Then, 50 ml of water was added to the residue and the mixture was further concentrated to obtain about 50 ml of the residue. The product was extracted with 100 ml of chloroform. The chloroform layer was washed with an aqueous solution of potassium carbonate until ceasing the generation of carbon dioxide gas and dehydrated over sodium sulfate and chloroform was distilled off under a reduced pressure to obtain 42.0 g of 6-phenoxy-2-picoline-N-oxide ($n_D^{20} = 1.5978$) (yield: 97.2% based on the starting material picoline).

All of the resulting compound of 6-phenoxy-2-picoline-N-oxide was added to 45.0 g of acetic anhydride and the mixture was refluxed for 15 minutes to react them. After the reaction, acetic anhydride and the by-product of acetic acid were distilled off under a reduced pressure and the resulting crude product was distilled under a reduced pressure to obtain 44.5 g of the object compound (yield: 89.6% based on the stating material of picoline).

Structure

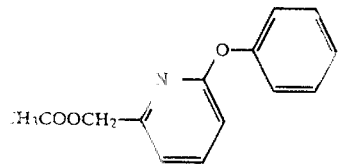

Physical property

Boiling point: 141°–142° C./0.4 mmHg
$N_D^{20} = 1.5586$

Elementary analysis

|  | C | H | N |
|---|---|---|---|
| Found (%) | 70.60 | 5.48 | 5.85 |
| Calculated (%) | 69.12 | 5.39 | 5.76 |

NMR spectrum

| ∂ ppm, CCl₄: | 1.91(s, 3H), 4.89(s, 2H), 6.67(1H, d, J = 8.0 Hz), 7.50(1H, dd, J = 8.0 Hz), 6.85–7.30(6H, m) |
|---|---|

EXAMPLE 2

Preparation of 6-phenoxypyridine-2-methanediol diacetate (Compound No. 2: Formula VII)

In accordance with the process of Example 1, 23.1 g. of 6-phenoxypyridine-2-methanol acetate was oxidized by using hydrogen peroxide-glacial acetic acid, to obtain 21.0 g of 6-phenoxypyridine-2-methanol acetate-N-oxide ($n_D^{20} = 1.5926$) (yield: 85.0%).

All of the 6-phenoxypyridine-2-methanol acetate-N-oxide was added to 17.3 g of acetic anhydride and the mixture was refluxed for 30 minutes to react them. The reaction mixture was cooled and extracted with 300 ml of ether and the ether layer was washed with 100 ml of water and with an aqueous solution of sodium bicarbonate to be neutral. The ether layer was dried over sodium sulfate and ether was distilled off and the resulting crude product was distilled under a reduced pressure to obtain 21.6 g of the object compound (yield: 74.8%).

Structure

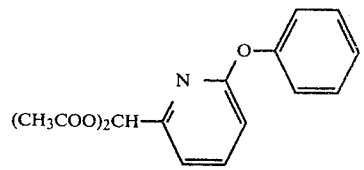

Physical property

Boiling point: 169°–170° C./0.45 mmHg
$n_D^{20} = 1.5434$

Elementary analysis

|  | C | H | N |
|---|---|---|---|
| Found (%) | 64.40 | 5.05 | 4.51 |
| Calculated (%) | 63.78 | 5.02 | 4.65 |

NMR spectrum

| ∂ ppm, CCl₄: | 1.92(6H, s), 6.78(1H, d, J = 8.0 Hz), 7.60(1H, dd, J = 8.0 Hz), 6.90–7.50(7H, m) |
|---|---|

EXAMPLE 3

Preparation of 6-phenoxypyridine-4-methanol acetate (Compound No. 3: Formula VIII)

In accordance with the process of Example 1, 37 g of 6-phenoxy-4-picoline was oxidized by using hydrogen peroxide-glacial acetic acid to obtain 28.2 g of 6-phenoxypyridine-4-methanol-N-oxide. Then, 28.2 g of 6-phenoxypyridine-4-methanol-N-oxide and 28.6 g of acetic anhydride were added to 400 ml of dioxane and the mixture was refluxed for 5 hours to react them.

In accordance with the process of Example 1, the reaction mixture was worked up and the product was distilled under a reduced pressure to obtain 13.6 g of the object compound (yield: 30%).

Structure

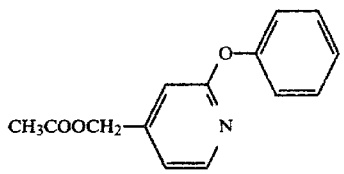

NMR spectrum

| ∂ ppm, CCl$_4$: | 2.05(3H, s), 5.02(2H, s), 7.90(1H, d, J = 6.0 Hz), 6.58–7.60(7H, m) |
| --- | --- |

EXAMPLE 4

Preparation of 4-phenoxypyridine-2-methanol acetate (Compound No. 5: Formula X)

In accordance with the process of Example 1, 37 g of 4-phenoxy-2-picoline was oxidized by using hydrogen peroxide-glacial acetic acid to obtain 39.4 g of 4-phenoxypyridine-2-methanol-N-oxide.

All of the 4-phenoxypyridine-2-methanol-N-oxide was added to 45.0 g of acetic anhydride and the mixture was refluxed for 15 minutes to react them. After the reaction, acetic anhydride and the by-product of acetic acid were distilled off under a reduced pressure and the resulting crude product was distilled under a reduced pressure to obtain 40 g of the object compound (yield: 88%).

Structure

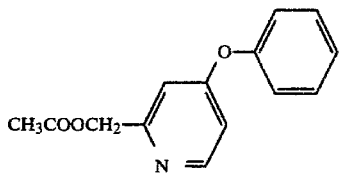

NMR spectrum

| ∂ ppm, CCl$_4$: | 2.00(3H, s), 5.01(2H, s) 6.32–7.50(7H, m), 8.23(1H, d, J = 6.0 Hz) |
| --- | --- |

We claim:

1. Phenoxypyridine derivatives having the formula $$(CH_3COO)_nCH_{3-n}R \quad (I)$$

wherein R represents

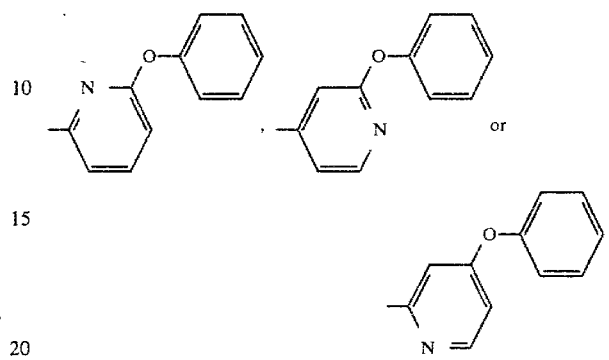

and n is 1 or 2.

2. Phenoxypyridine derivatives according to claim 1 which has the formula

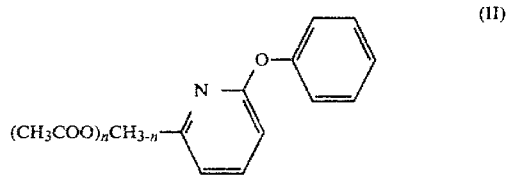

(II)

wherein n is 1 or 2.

3. A phenoxypyridine derivative according to claim 2 which has the formula

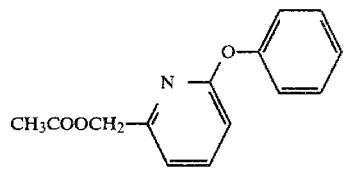

4. A phenoxypyridine derivative according to claim 2 which has the formula

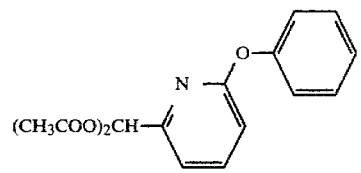

* * * * *